United States Patent
Hausen (10) Patent No.: US 7,744,610 B2
(45) Date of Patent: Jun. 29, 2010

(54) SYSTEM FOR CLOSING A TISSUE STRUCTURE FROM INSIDE

(75) Inventor: Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 543 days.

(21) Appl. No.: 11/780,648

(22) Filed: Jul. 20, 2007

(65) Prior Publication Data
US 2008/0017691 A1    Jan. 24, 2008

Related U.S. Application Data

(63) Continuation-in-part of application No. 11/093,003, filed on Mar. 28, 2005, now Pat. No. 7,344,544.

(51) Int. Cl.
*A61B 17/10* (2006.01)
(52) U.S. Cl. ........................ 606/142; 606/139
(58) Field of Classification Search ............ 606/139, 606/142–143, 151–158; 623/1.23; 227/175.1–182.1
See application file for complete search history.

(56) References Cited

U.S. PATENT DOCUMENTS

| | | |
|---|---|---|
| 3,526,228 A | 9/1970 | Lyng |
| 3,958,576 A | 5/1976 | Komiya |
| 4,317,451 A | 3/1982 | Cerwin et al. |
| 4,509,518 A | 4/1985 | McGarry et al. |
| 4,836,204 A | 6/1989 | Landymore et al. |
| 5,007,921 A | 4/1991 | Brown |
| 5,026,390 A | 6/1991 | Brown |
| 5,042,707 A | 8/1991 | Taheri |
| 5,156,609 A | 10/1992 | Nakao et al. |
| 5,201,745 A | 4/1993 | Tayot et al. |
| 5,222,961 A | 6/1993 | Nakao et al. |
| 5,411,523 A | 5/1995 | Goble |
| 5,413,584 A | 5/1995 | Schulze |
| 5,591,177 A | 1/1997 | Lehrer |
| 5,662,681 A | 9/1997 | Nash et al. |

(Continued)

FOREIGN PATENT DOCUMENTS

WO    WO-99/62408    12/1999

(Continued)

OTHER PUBLICATIONS

"VasoStasis (TM) Vascular Closure System 510(k) Notification", (Oct. 22, 2004).

(Continued)

*Primary Examiner*—Darwin P Erezo
*Assistant Examiner*—Gregory Anderson
(74) *Attorney, Agent, or Firm*—Brian A. Schar (57) ABSTRACT

A method for closing an aneurysm in a blood vessel may utilize a staple having two or more tines, where those tines are oriented at least partially in the proximal direction. The method may include advancing the staple through the vasculature to a location within the aneurysm, plastically deforming the staple to a splayed configuration, penetrating at least one said tine of the staple in that splayed configuration into tissue in proximity to the neck of the aneurysm, and plastically deforming the staple to a closed configuration to close the aneurysm.

7 Claims, 10 Drawing Sheets

U.S. PATENT DOCUMENTS

| | | | |
|---|---|---|---|
| 5,674,231 A | 10/1997 | Green et al. |
| 5,695,504 A | 12/1997 | Gifford, III et al. |
| 5,728,109 A | 3/1998 | Schulze et al. |
| 5,792,094 A | 8/1998 | Stevens et al. |
| 5,810,846 A | 9/1998 | Virnich et al. |
| 5,843,124 A | 12/1998 | Hammerslag |
| 5,861,005 A | 1/1999 | Kontos |
| 5,902,310 A | 5/1999 | Foerster et al. |
| 5,910,155 A | 6/1999 | Ratcliff et al. |
| 6,022,372 A | 2/2000 | Kontos |
| 6,042,584 A | 3/2000 | Pierson, III |
| 6,149,660 A | 11/2000 | Laufer et al. |
| 6,197,042 B1 | 3/2001 | Ginn et al. |
| 6,269,819 B1 | 8/2001 | Oz et al. |
| 6,277,140 B2 | 8/2001 | Ginn et al. |
| 6,302,898 B1 | 10/2001 | Edwards et al. |
| 6,322,580 B1 | 11/2001 | Kanner |
| 6,348,064 B1 | 2/2002 | Kanner |
| 6,355,050 B1 | 3/2002 | Andreas et al. |
| 6,368,341 B1 | 4/2002 | Abrahamson |
| 6,371,974 B1 | 4/2002 | Brenneman et al. |
| 6,391,048 B1 | 5/2002 | Ginn et al. |
| 6,451,031 B1 | 9/2002 | Kontos |
| 6,461,364 B1 | 10/2002 | Ginn et al. |
| 6,482,224 B1 | 11/2002 | Michler et al. |
| 6,506,210 B1 | 1/2003 | Kanner |
| 6,508,828 B1 | 1/2003 | Akerfeldt et al. |
| 6,524,321 B2 | 2/2003 | Kanesaka |
| 6,524,326 B1 | 2/2003 | Zhu et al. |
| 6,533,762 B2 | 3/2003 | Kanner et al. |
| 6,540,735 B1 | 4/2003 | Ashby et al. |
| 6,623,510 B2 | 9/2003 | Carley et al. |
| 6,626,918 B1 | 9/2003 | Ginn et al. |
| 6,632,238 B2 | 10/2003 | Ginn et al. |
| 6,676,685 B2 | 1/2004 | Pedros et al. |
| 6,695,867 B2 | 2/2004 | Ginn et al. |
| 6,712,828 B2 | 3/2004 | Schraft et al. |
| 6,719,777 B2 | 4/2004 | Ginn et al. |
| 6,726,704 B1 | 4/2004 | Loshakove et al. |
| 6,743,239 B1 | 6/2004 | Kuehn et al. |
| 6,743,248 B2 | 6/2004 | Edwards et al. |
| 6,749,621 B2 | 6/2004 | Pantages et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,942,674 B2 | 9/2005 | Belef |
| 7,111,768 B2 | 9/2006 | Cummins et al. |
| 7,399,310 B2 * | 7/2008 | Edoga et al. | 606/219 |
| 7,597,706 B2 * | 10/2009 | Kanner et al. | 606/219 |
| 2001/0007077 A1 | 7/2001 | Ginn et al. |
| 2001/0021855 A1 | 9/2001 | Levinson |
| 2001/0021856 A1 | 9/2001 | Bolduc et al. |
| 2001/0023352 A1 | 9/2001 | Gordon et al. |
| 2002/0072768 A1 | 6/2002 | Ginn |
| 2002/0082641 A1 | 6/2002 | Ginn et al. |
| 2002/0133193 A1 | 9/2002 | Ginn et al. |
| 2002/0151921 A1 | 10/2002 | Kanner |
| 2002/0156495 A1 | 10/2002 | Brenneman et al. |
| 2002/0193808 A1 | 12/2002 | Belef et al. |
| 2003/0078598 A1 | 4/2003 | Ginn et al. |
| 2003/0097140 A1 | 5/2003 | Kanner |
| 2003/0100920 A1 | 5/2003 | Akin et al. |
| 2003/0109890 A1 | 6/2003 | Kanner et al. |
| 2003/0158577 A1 | 8/2003 | Ginn et al. |
| 2003/0158578 A1 | 8/2003 | Pantages et al. |
| 2004/0002681 A1 | 1/2004 | McGuckin, Jr. et al. |
| 2004/0010285 A1 | 1/2004 | Carley et al. |
| 2004/0059375 A1 | 3/2004 | Ginn et al. |
| 2004/0073236 A1 | 4/2004 | Carley et al. |
| 2004/0073255 A1 | 4/2004 | Ginn et al. |
| 2004/0092965 A1 | 5/2004 | Parihar |
| 2004/0153122 A1 | 8/2004 | Palermo |
| 2004/0153123 A1 | 8/2004 | Palermo et al. |
| 2004/0176798 A1 | 9/2004 | Epstein et al. |
| 2004/0225301 A1 | 11/2004 | Roop et al. |
| 2005/0021054 A1 | 1/2005 | Ainsworth et al. |
| 2005/0080435 A1 | 4/2005 | Smith et al. |
| 2005/0090834 A1 | 4/2005 | Chiang et al. |
| 2005/0090843 A1 | 4/2005 | Bolduc |
| 2005/0131460 A1 | 6/2005 | Gifford, III et al. |
| 2005/0171561 A1 | 8/2005 | Songer et al. |
| 2005/0187613 A1 | 8/2005 | Bolduc et al. |
| 2006/0200197 A1 | 9/2006 | Brenzel et al. |
| 2007/0010854 A1 | 1/2007 | Cummins |
| 2008/0177300 A1 | 7/2008 | Mas et al. |

FOREIGN PATENT DOCUMENTS

| | | |
|---|---|---|
| WO | WO-00/07640 | 2/2000 |
| WO | WO-00/56223 | 9/2000 |
| WO | WO-00/56227 | 9/2000 |

OTHER PUBLICATIONS

"Summary of Safety and Effectiveness Data (EVS (TM) Vascular Closure System)", (Nov. 3, 2004).

"The EVS(TM) Vascular Closure System by Angiolink", *Business Briefing: US Cardiology 2004*, (2004).

"Closure and Assisted-Compression Device Update", *Endovascular Today*, (Apr. 2002),22.

*Notification of Transmittal of the International Search Report and the Written Opinion of the International Searching Authority*, PCT/US/2006004763, Aug. 20, 2007.

*International Search Report*, PCT/US/2006004763, Aug. 20, 2007.

*Written Opinion of the International Searching Authority*, PCT/US/2006004763, Aug. 20, 2007.

* cited by examiner

SYSTEM FOR CLOSING A TISSUE STRUCTURE FROM INSIDE

This patent application is a continuation-in-part of U.S. patent application Ser. No. 11/093,003, filed on Mar. 28, 2005, now U.S. Pat. No. 7,344,544,which is hereby incorporated by reference in its entirety.

FIELD OF THE INVENTION

The present invention relates generally to a system for closing a tubular tissue structure, and more specifically to a system for closing a vascular aneurysm from the inside.

BACKGROUND

An aneurysm is an abnormal ballooning or dilation of a blood vessel. A cerebral aneurysm is an aneurysm in an artery or vein in the brain. Cerebral aneurysms are more common in adults than in children and more common in women than in men. Cerebral aneurysms commonly arise at the bifurcations of major arteries; most cerebral aneurysms arise on the circle of Willis (where several arteries join near the bottom of the brain) or the middle cerebral artery (MCA) bifurcation.

A common complication of a cerebral aneurysm is rupture, which results in profuse bleeding and causes serious complications including hemorrhagic stroke, permanent nerve damage, hydrocephalus, vasospasm, and/or death. Another complication of a cerebral aneurysm is stroke. Blood pools in the aneurysm, where it becomes isolated from the flow of blood in the brain and subsequently clots. Clots of various sizes can then break off, escape from the cerebral aneurysm into the cerebral vasculature and lodge downstream, causing a stroke.

A variety of options exist for treating cerebral aneurysms. As one example, the aneurysm is clipped from outside before or after it bursts to isolate the aneurysm from the vasculature. However, such clipping requires highly invasive surgical intervention in the brain through the skull. Further, clipping the aneurysm after it bursts does nothing to prevent the potentially-fatal consequences of rupture. It is preferable to treat the aneurysm before it bursts, because patients who receive treatment for an unruptured aneurysm generally require less therapy and recover more quickly. As an example of such treatment, the aneurysm is filled with wire coils. Conventional catheterization techniques are used to insert a catheter into the patient's vasculature at a location outside the brain, such as the groin or the neck, and advance the catheter to the aneurysm using angiography, after which the coils are delivered through the catheter to the aneurysm. The coils fill the aneurysm before it bursts, block it from circulation, and cause the blood to clot. However, the coils may become dislodged from the aneurysm and enter the vasculature, causing stroke in the same manner as blood clots that become dislodged from the aneurysm. Further, smaller clots may still break off and escape from the cerebral aneurysm, resulting in stroke.

BRIEF DESCRIPTION OF THE DRAWINGS

The use of the same reference symbols in different figures indicates similar or identical items.

DETAILED DESCRIPTION

Closure System

Figure 1:
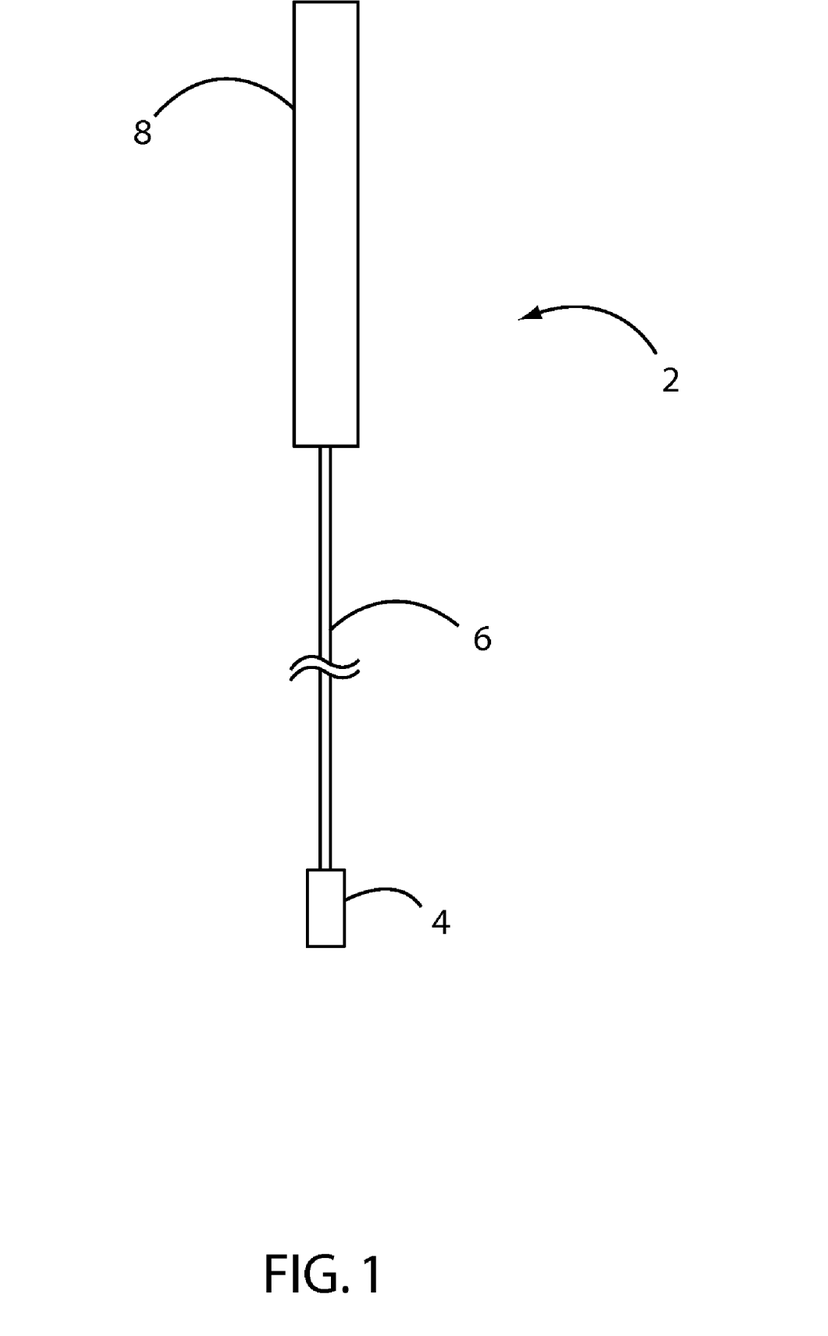
FIG. 1 is a schematic view of an aneurysm closure system that includes an end effector, a shaft and a handle.
Figure 7:
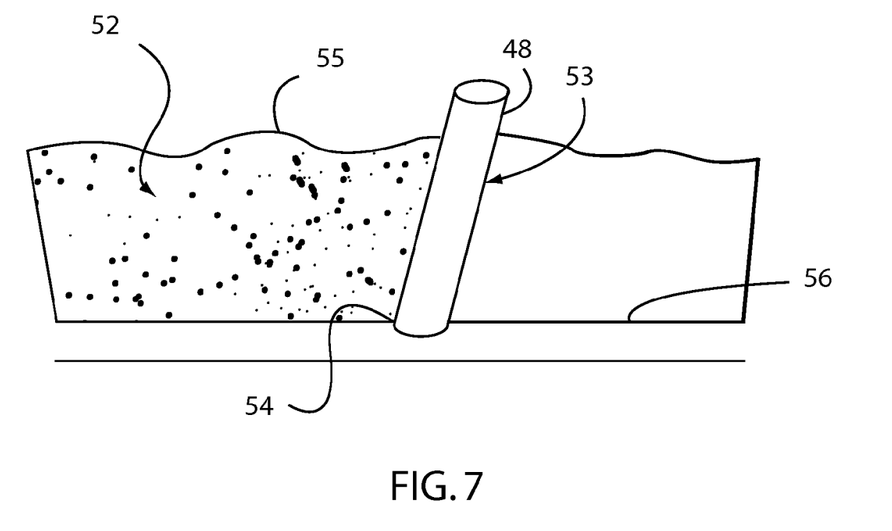
FIG. 7 is a schematic view of tissue having a catheterization sheath positioned therein to provide access to a blood vessel such as the femoral artery.

Referring to FIG. 1, an closure system 2 includes an end effector 4 connected to a shaft 6, which in turn is connected to a handle 8. The end effector 4 may be one or more separate components that are connected to the shaft 6, or may be fabricated integrally with the distal end of the shaft 6. At least part of the shaft 6 is flexible, to allow the shaft 6 to be advanced through the vasculature of a patient to a vascular aneurysm. The shaft 6 of the closure system 2 may be or may include a steering catheter or steering mechanism. Alternately, the shaft 6 is a catheter without steering features, where that catheter follows a previously-placed guidewire to the site of the opening in the tissue of the heart. Alternately, the shaft 6 is any other structure, mechanism or combination thereof that is suitable for advancing the end effector 4 through the vasculature to the site of the opening in the tissue of the heart. The shaft 6 may include a lumen or other structure configured to receive a guidewire (not shown), such that the shaft 6 can be advanced along that guidewire. Referring also to FIG. 7, the end effector 4 is sized to pass through a standard sheath 48 placed in a passage 53 in tissue 52 for a standard catheterization procedure.

Figure 2:
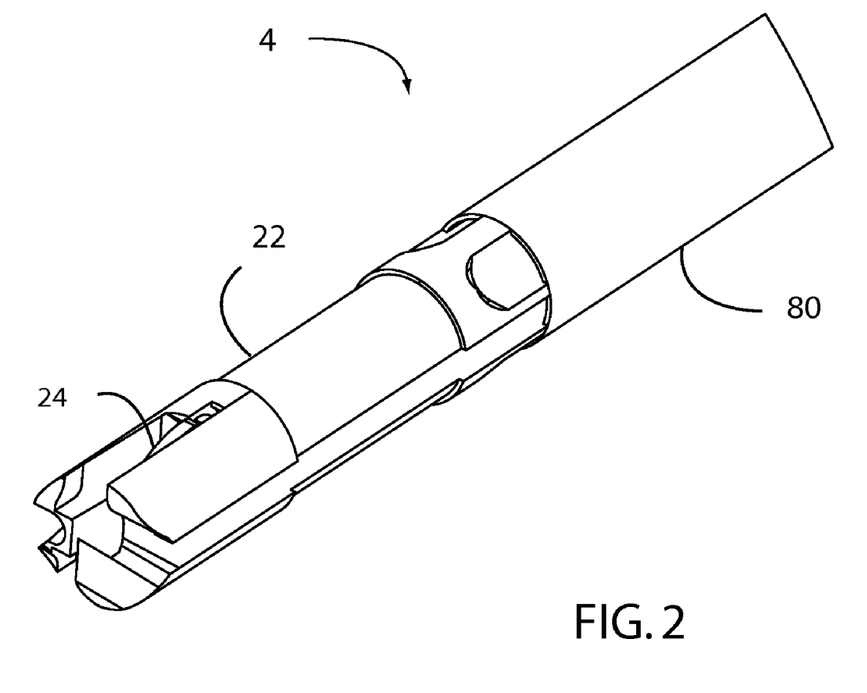
FIG. 2 is a perspective view of the end effector of FIG. 1 in a first configuration.
Figures 3, 4:
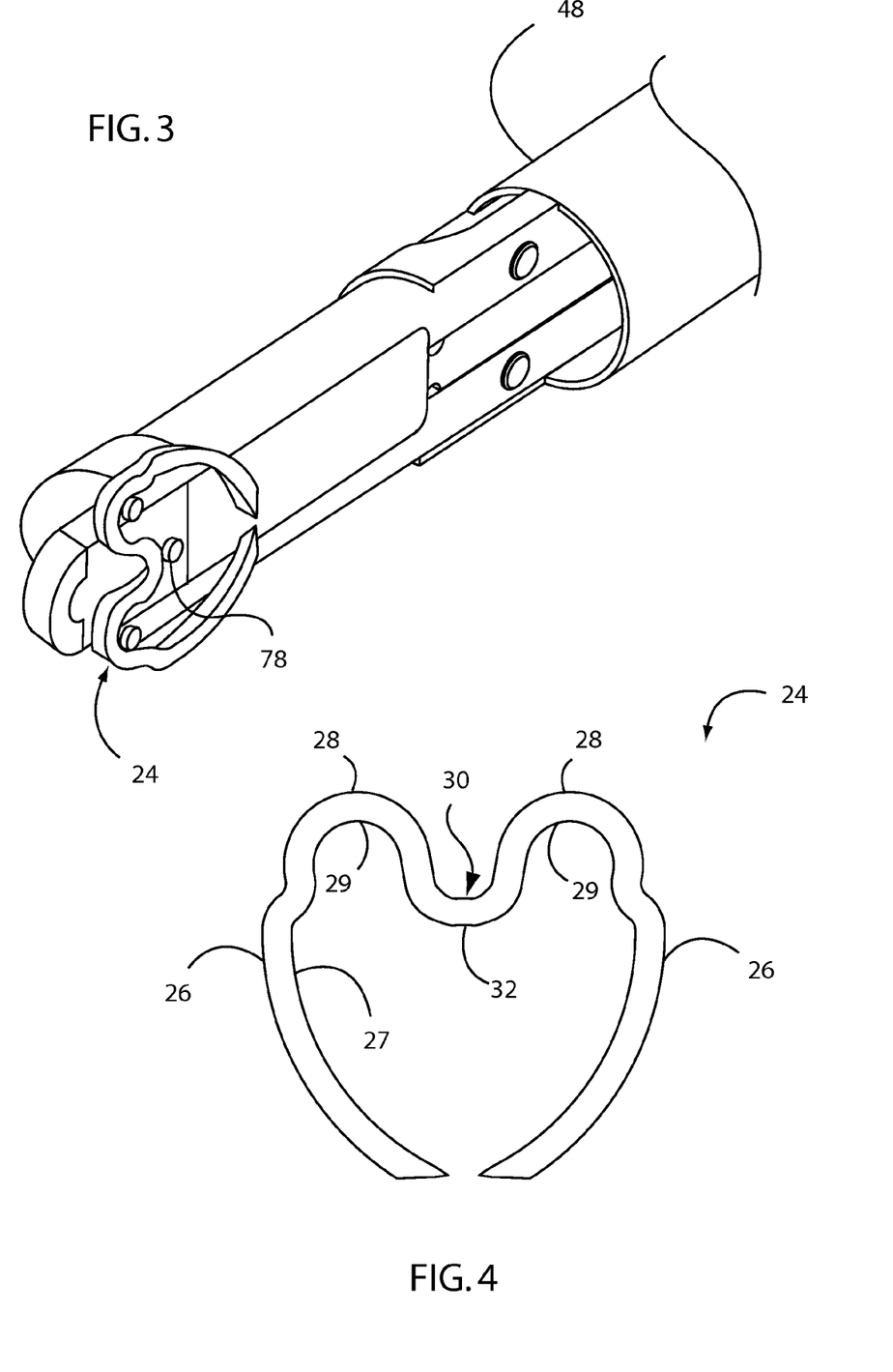
FIG. 3 is a perspective cross-section view of the end effector of FIG. 1 in a first configuration.
FIG. 4 is a side view of a staple in a first configuration.

The end effector 2 may include a housing 22. The housing 22 advantageously is blunt at its distal end. However, the housing 22 may be configured in any other suitable manner. The housing 22 may be fabricated from any suitable material. Referring to FIGS. 2-3, a staple 24 initially may be positioned entirely within a space inside the housing 22 of the end effector 2. As another example, at least the distal end of the staple 24 and/or other portion of the staple 24 may extend out of the distal end of the housing 22 and/or other portion of the housing 22. If so, the portion of the staple 24 that extends out of the housing 22 is generally blunt. For example, the distal end of the staple 24 may extend out of the housing 22, and may be generally blunt. Alternately, the staple 24 may be positioned differently within the end effector 4, or may be positioned at the end of the end effector 4 or other position on the end effector 4 rather than within the end effector 2. The staple 24 may be sized and shaped in any suitable manner. As one example, referring also to FIG. 4, the staple 24 may have a curved M-shape. However, the staple 24 may have any other suitable shape. The staple 24 may have two tines 26, each extending at least partially in the proximal direction. The tines 26 may be curved, and may each have a shape and radius of curvature such that the tines 26 are generally not parallel to one another. The radius of curvature may be substantially coincident with the path of travel of the tines 26 during closure of the staple 24. The staple 24 may be substantially bilaterally symmetrical, although it may be asymmetrical if desired. The staple 24 may be a substantially continuous solid. As used in this document, the term "continuous solid" means that a structure has no slots, holes, apertures or other enclosed or bounded openings defined therein.

The proximal end of each tine 26 may have a substantially pointed or sharpened proximal end. However, the proximal ends of the tines 26 need not be pointed or sharpened, particularly if the cross-sectional area of each tine 26 is small. Advantageously, each tine 26 has a single proximal end that is not bifurcated or otherwise forked or split. The body of the staple 24 extends distally from the proximal end of one tine 26 and curves or angles toward the longitudinal centerline of the staple 24. This curve may extend outward from the longitudinal centerline of the staple 24, then toward the longitudinal centerline of the staple 24. Alternately, the tine 26 may curve differently. The body of the staple 24 reaches a peak 28, then extends proximally and toward the longitudinal centerline of the staple 24. The body of the staple 24 then reaches a trough 30, then extends distally and away from the longitudinal centerline of the staple to a second peak 28. The body of the staple 24 continues proximally to form the second tine 26, and ends at the proximal end of the second tine 26. Alternately, the staple 24 may be shaped differently. A valley 29 is the area on the staple 24 on the other side of the staple 24 from a peak 28. For example, where a peak 28 of the staple 24 includes a convex curve oriented distally, the corresponding valley 29 is a concave curve opening proximally. The staple 24 may be oriented in the housing 22

Figure 5:
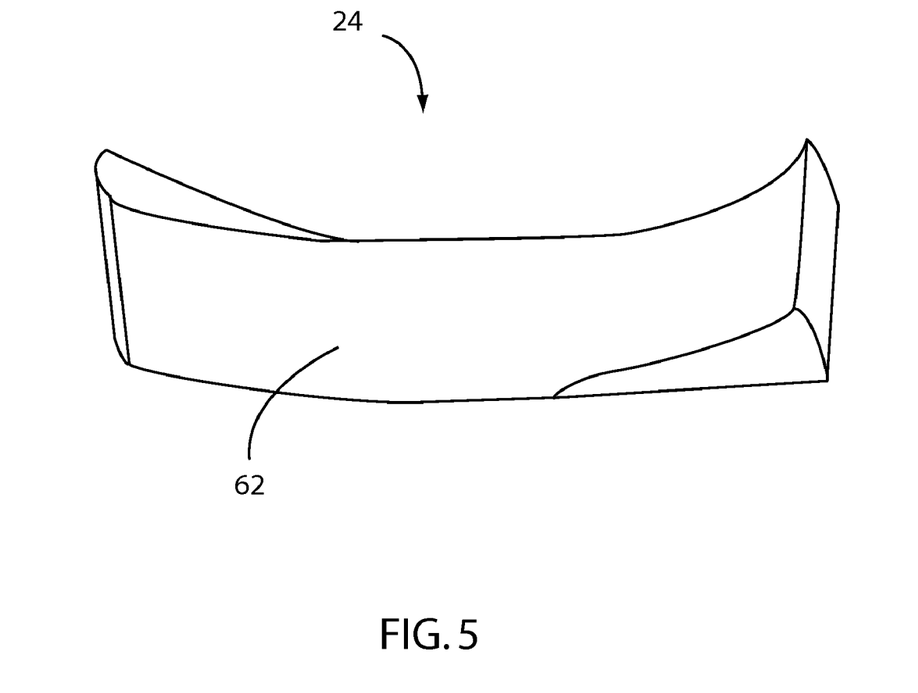
FIG. 5 is a top view of an exemplary staple.

The staple 24 may lie substantially in a single plane. That is, the staple 24 may be shaped such that a single plane extends through and substantially bisects the entire staple 24. Alternately, the staple 24 does not lie substantially in a single plane. The longitudinal and lateral dimensions of the staple 24 overall may both be substantially larger than the height of the staple 24. Alternately, the staple 24 may be sized differently. Referring also to FIG. 5, the distal surface 62 of the staple 24 optionally may be curved relative to a plane perpendicular to the longitudinal axis of the staple 24. For example, the distal surface 62 of the staple 24 may take the shape of a twisted plane. The distal surface 62 of the staple 24 may be twisted such that a line perpendicular to that distal surface 62 on one side of the longitudinal centerline of the staple 24 is skewed relative to a line perpendicular to that distal surface 62 on the other side of the longitudinal centerline of the staple 24, and both such lines are skewed relative to the longitudinal centerline of the staple 24.

Figure 5A:
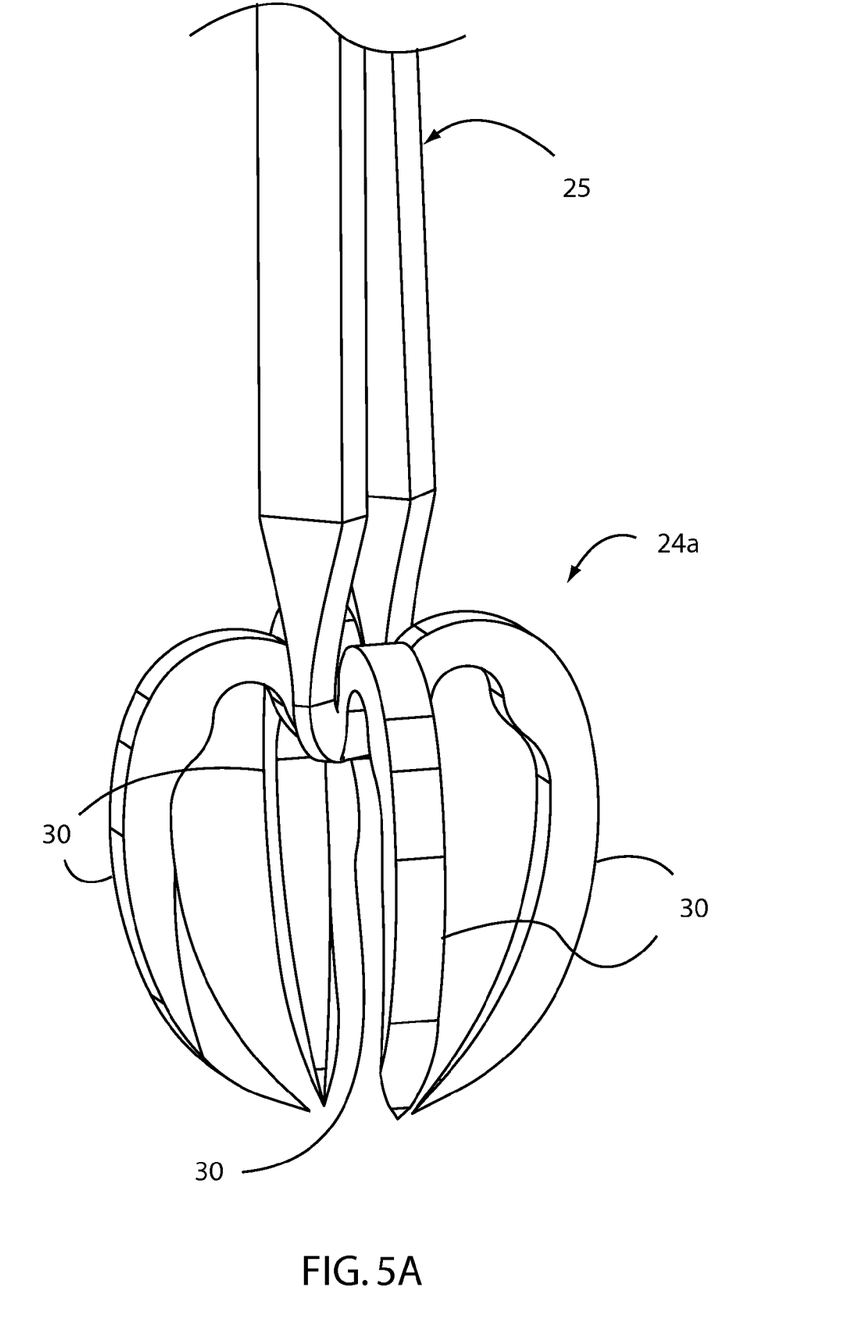
FIG. 5A is a perspective view of another exemplary staple in an initial configuration.
Figure 5B:
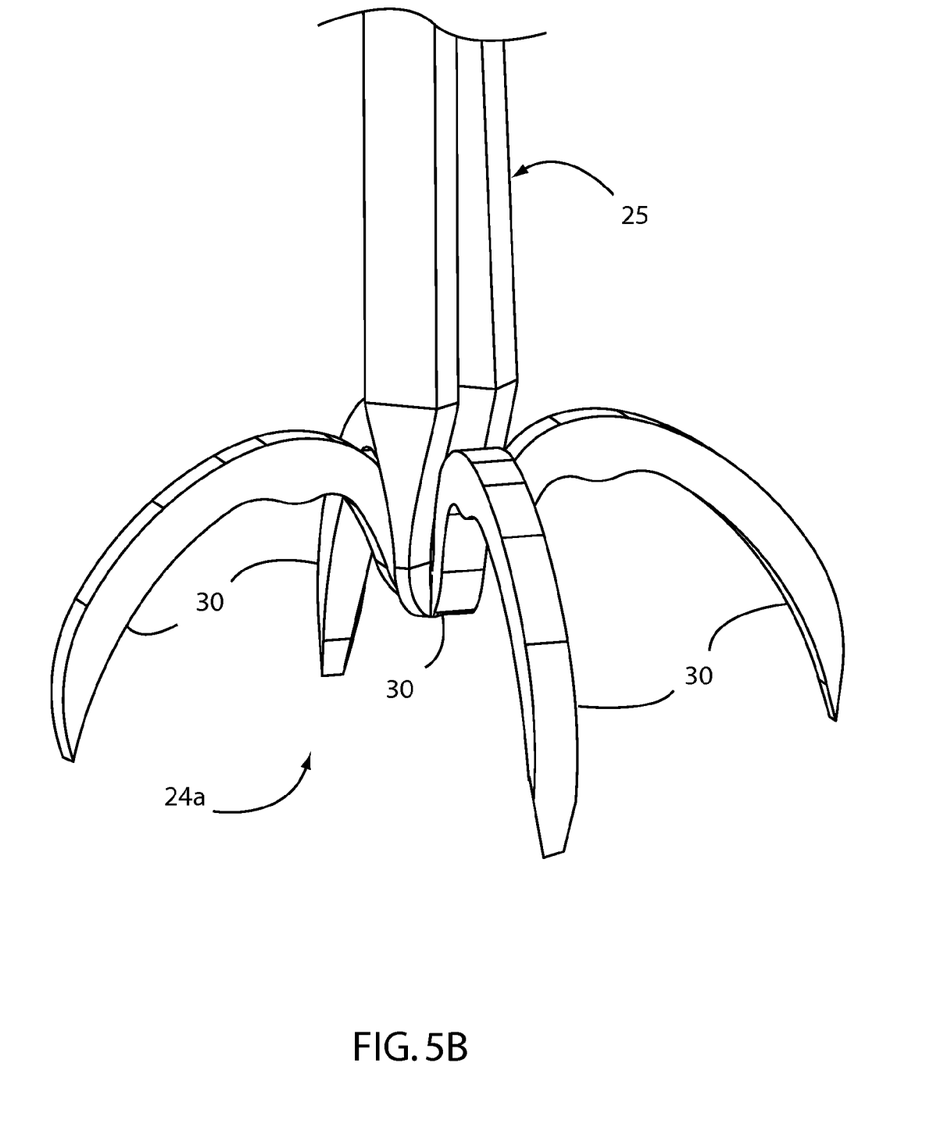
FIG. 5B is a perspective view of the staple of FIG. 5A in a splayed configuration.
Figure 5C:
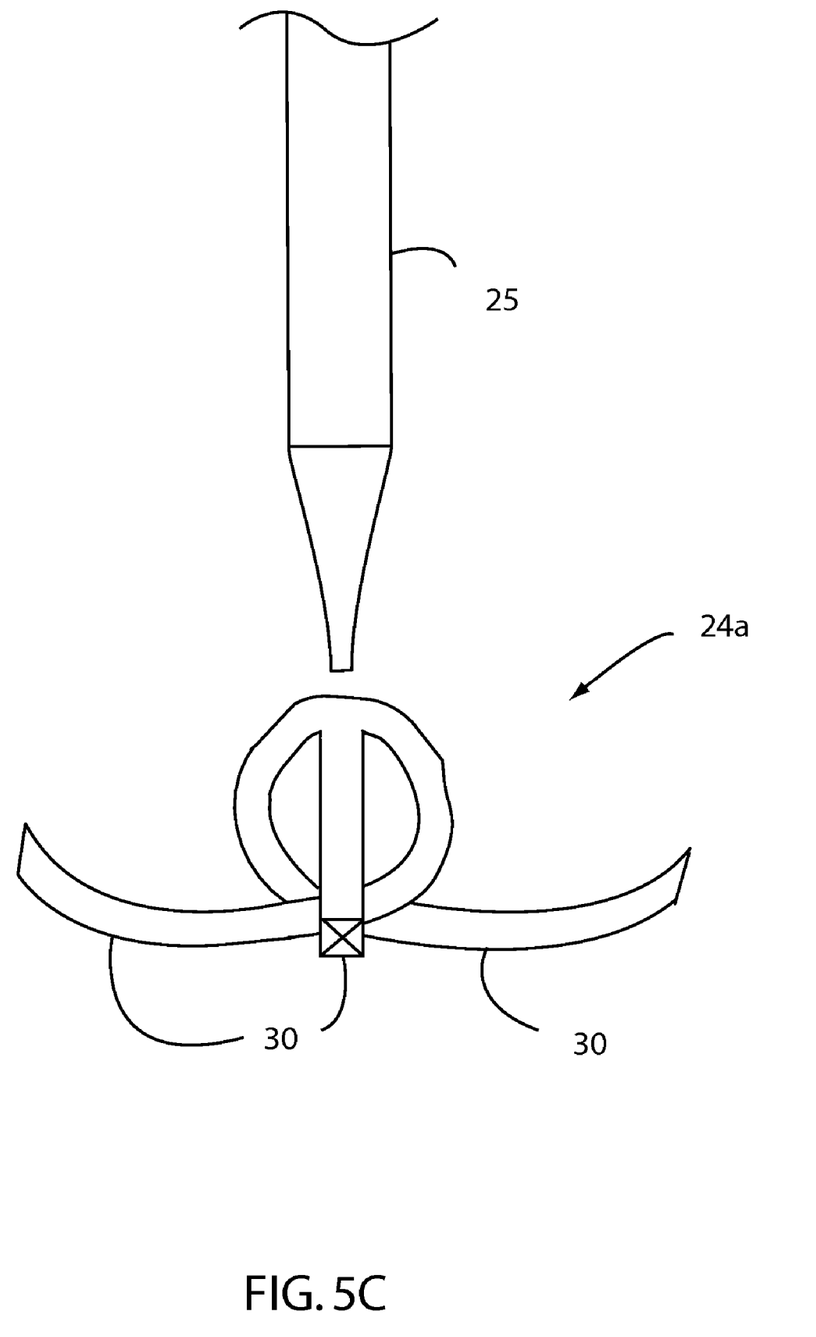
FIG. 5C is a side view of the staple of FIG. 5A in a closed configuration.

Referring to FIGS. 5A-5C, another exemplary embodiment of a staple 24a is shown, in a first, initial position. The staple 24a may include four tines 26. Alternately, three tines 26, or more than four tines 26, may be used. Advantageously, the staple 24a may be fabricated substantially as two staples 24, each substantially as described above with regard to FIG. 5, oriented at substantially right angles to one another and connected at the trough 30 of each staple 24. The junction of the troughs 30 of the staples 24 may be characterized as the trough 30 of the staple 24a. Viewed on end, the staple 24a may be generally X-shaped. However, the staple 24a may be shaped differently. The staple 24a may be fabricated integrally, or may be fabricated from two or more individual staples 24 that subsequently are fixed together. Alternately, where the staple 24a includes an odd number of tines 26, each tine 26 may be shaped the same as or similar to one-half of the staple 24 described with regard to FIG. 5. Alternately, at least one tine 26 may be shaped differently. Advantageously, the staple 24a is a single one-piece structure. The staple 24a may be fabricated integrally with a holder 25, and may be frangible or otherwise separable from the holder 25 at a suitable time during or after deployment.

The staple 24 may be plastically deformable. If so, the staple 24 may be fabricated from stainless steel, titanium or any other suitable plastically-deformable material. Alternately, the staple 24 may be elastically deformable. If so, the staple 24 may be fabricated from nickel-titanium alloy or any other suitable elastic or superelastic material. The staple 24 may be fabricated from a single wire or other piece of material, having a rectangular, circular or other cross-section. The cross-section of the staple 24 may be substantially constant along the entire staple 24, or may vary at different locations along the staple 24. For example, the cross-sectional area of the staple 24 at certain locations may be less than at other locations, in order to promote bending in those locations having a lesser cross-sectional area.

Figure 6:
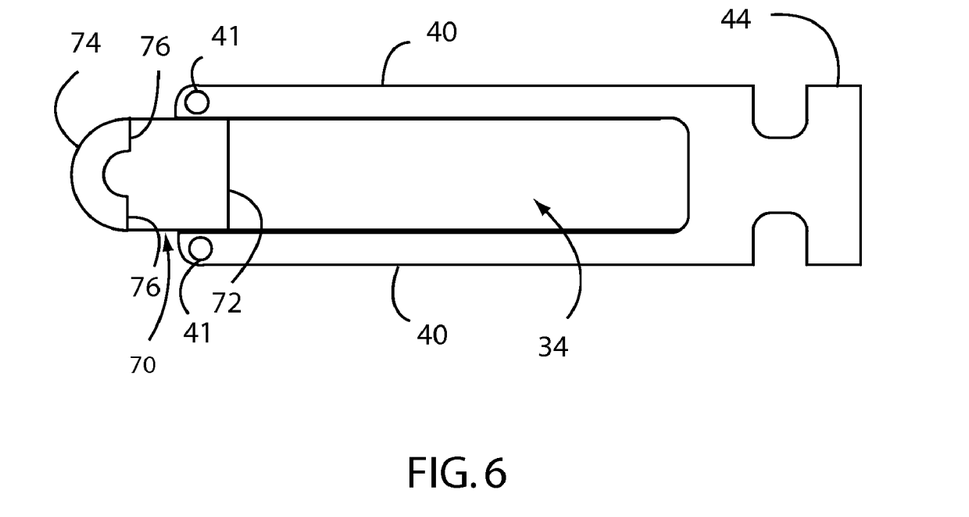
FIG. 6 is a side view of a driver and paddles that are utilized within the end effector.

Referring also to FIG. 6, the end effector 4 includes a driver 34. The distal end of the driver 34 may be located distal to the staple 24, and may be movable relative to the staple 24 such as by sliding. The distal end of the driver 34 may be blunt, particularly if at least the distal end of the driver 34 is positioned outside the housing 22. As another example, the driver 34 may be positioned entirely within the housing 22. The housing 22 may be at least partially hollow in order to accommodate the driver 34. Advantageously, the housing 22 includes a passage 36 therein along which at least part of the driver 34 may slide or otherwise move. At least part of the passage 36 may guide the driver 34 during at least part of its motion.

The driver 34 may be configured in any suitable manner. As one example, the driver 34 is an elongated member having a depression 70 defined near the distal end thereof. A raised area 74 is located distal to the depression 70, where the raised area 74 may have a thickness the same as or different from the portion of the driver 34 proximal to the depression 70. A portion of the staple 24 may be positioned within the depression when the end effector 4 is in an initial configuration. The portion of the driver excluding the depression 70 may have a thickness substantially equal to that of the staple 24. A wall 72 defines the proximal end of the depression 70, where the wall 72 extends at generally a right angle, or a different angle or curvature, from the surface of the depression 70. The raised area 74 may extend completely to the distal end of the driver 34. The proximal end of the raised area 74 may be bifurcated, where each bifurcation 76 is oriented least partially in the proximal direction and configured to engage a corresponding peak 28 of the staple 24. Alternately, the distal end of the driver 34 is shaped differently. Optionally, the staple 24 may be fabricated integrally with the driver 34. If so, the staple 24 is frangible from the driver 34, such that the staple 24 separates from the driver 34 at a suitable time during or after deployment. Fabrication of the staple 24 integrally with the driver 34 may facilitate manufacturing. Alternately, the driver 34 may be shaped and/or configured differently, in any other suitable manner.

Figure 6A:
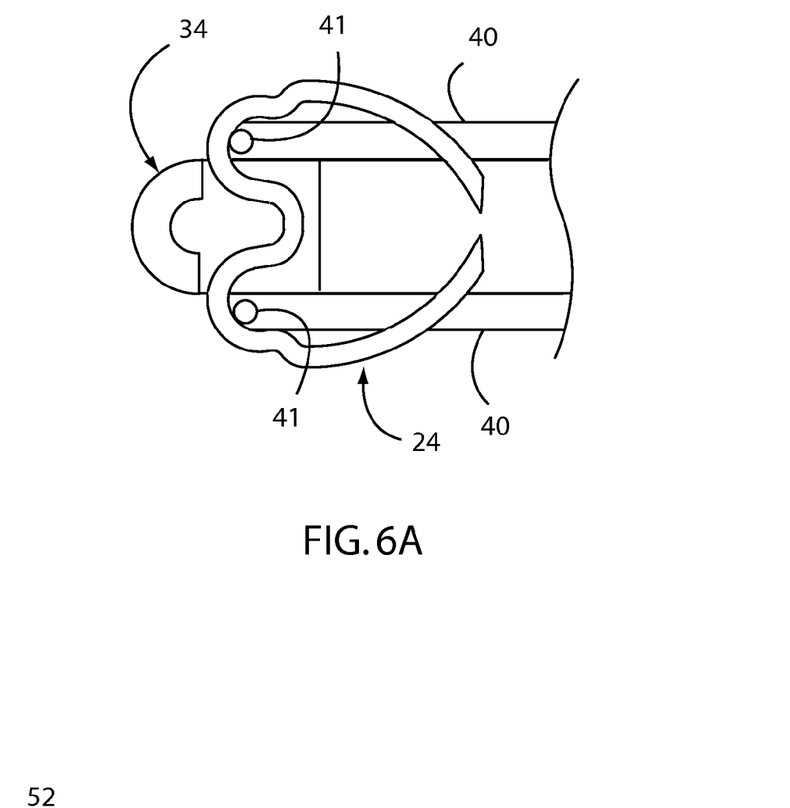
FIG. 6A is a side view of the driver and paddles of FIG. 6, holding an exemplary staple.

Referring to FIG. 6A, a paddle assembly 38 may be located at least partially within the passage 36, at or near the distal end thereof. The paddle assembly 38 may include one or more paddles 40. As one example, two paddles 40 are utilized, and are generally parallel to one another and spaced apart from one another. The paddles 40 may be cantilevered from a base (not shown) of the paddle assembly 38. Alternately, the paddles 40 may be configured in any other suitable manner. At least one paddle 40 may include a post 41 at or near its distal end. Each post 41 may be substantially cylindrical. However, each post 41 may have any suitable shape. Each post 41 extends from a remainder of the paddle 40, and may be oriented substantially perpendicular to the longitudinal axis of the paddle 40. Alternately, at least one post may be oriented differently. When the end effector 4 is in an initial position, the distal end of the driver 34 may be in contact with, or in proximity to, the base 44 of the paddle assembly 38. The paddles 40 may be oriented in any suitable manner. As one example, the paddles 40 may be generally parallel to the driver 34. As another example, the paddle or paddles 40 may be angled or curved relative to the driver 34 such that relative motion of the paddles 40 and driver 34 causes deflection of the distal ends of the paddles 40 away from the longitudinal axis of the paddles 40.

Figure 8:
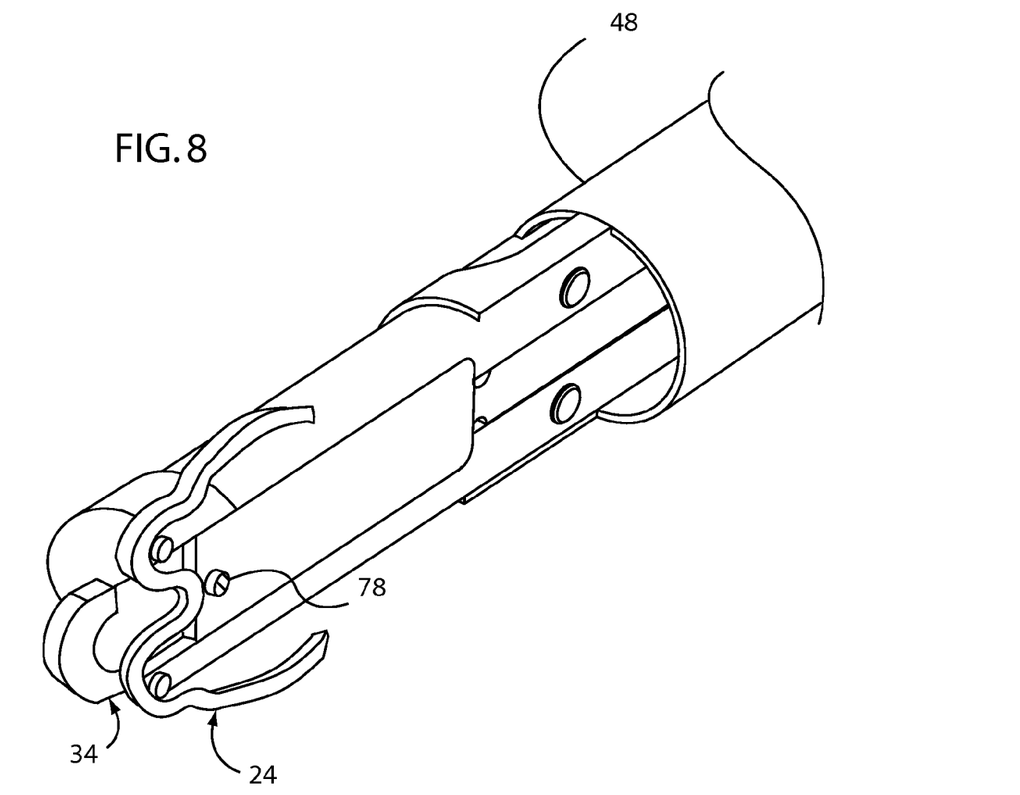
FIG. 8 is a perspective cutaway view of the end effector in a second configuration, as the staple is splayed.

Referring also to FIG. 8, an anvil 78 may extend inward from the housing 22 into the passage 36, such that at least part of the anvil 78 is located proximal to the trough 30 of the staple 24 when the end effector is in the initial position. Referring also to FIG. 3, only the portion of the anvil 78 that extends into the depression 70 is shown, for clarity. Alternately, the anvil 78 may be a separate component of the end effector 4 that may be fixed or movable relative to the housing 22. The anvil 78 may be shaped in any suitable manner. As one example, the anvil 78 may be generally cylindrical. As another example, the anvil 78 may be generally triangular.

Any other suitable mechanism or set of mechanisms may be used in lieu of the driver 34, paddle assembly 38 and/or anvil 78 described above. As one example, the mechanisms for splaying and closing staples that are disclosed in commonly-assigned U.S. patent application Ser. No. 11/686,320, filed on Mar. 14, 2007, which is hereby incorporated by reference in its entirety, may be used.

When the end effector 4 is in the initial position, the staple 24 is also in an initial position. In the initial position, each post 41 of each paddle 40 may be positioned proximal to a corresponding valley 29 of the staple 24, thereby substantially restraining the staple 24 against motion in the proximal direction. Further, when the end effector 4 is in the initial position, the raised area 74 of the driver 34 may be positioned distal to and against or in proximity to the peaks 28 of the staple 24, thereby substantially restraining the staple 24 against motion in the distal direction. In this way, the staple 24 may be held substantially in place while the end effector 4 is in the initial position. Alternately, the staple may be held substantially in place while the end effector 4 is in the initial position in any other suitable manner. For example, the staple 24 may be gently friction-fit against a portion of the housing 22.

Referring also to FIG. 1, the shaft 6 extends proximally from the end effector 4. The shaft 6 may be flexible or rigid. The shaft 6 may be articulated in at least one location, if desired. The shaft 6 may be steerable in any suitable manner, if desired. Referring also to FIG. 8, the shaft 6 and the end effector 4 both may be sized to pass through a standard sheath 48 used in a catheterization procedure. Optionally, the shaft 6 may include a cutaway, trough or other feature (not shown) to allow the guidewire (if any) used in the catheterization procedure to remain in place during actuation of the closure system 2.

The handle 8 is connected to the shaft 6, such as to the proximal end of the shaft 6. The shaft 6 may be fabricated such that the handle 8 is simply the proximal end of the shaft 6. Alternately, the shaft 6 and the handle 8 may be two separate items that are connected together in any suitable manner. The handle 8 may include any mechanism, mechanisms, structure or structures configured to actuate the end effector 4. For example, as described later in this document, the handle 8 may be configured to actuate the driver 34, paddle assembly 38 and/or the anvil 78. Thus, any suitable mechanism or mechanisms that are configured to actuate the driver 34, paddle assembly 38 and/or the anvil 78 may be used. As one example, a cable (not shown) may be connected to the driver 34, such that application of tension to that cable causes proximal motion of the driver 34. A cable may be directed around an axle, nose or other feature of the end effector 4 in order to convert proximal motion of the cable to distal motion of a mechanism to which that cable is connected. As another example, a rod (not shown) may be attached to the driver 34, extending through the shaft 6 to the handle 8. The rod may be rigid enough to transmit force, and may be flexible enough to move along the shaft 6 where the shaft 6 is flexible. Alternately, the driver 34, and/or any other suitable component of the end effector 4, may extend through the shaft 6 to the handle 8, in order to be actuated directly by the handle 8, and may connect directly to a mechanism, mechanisms, structure or structures in the handle 8 configured to actuate the end effector 4.

The handle 8 may also include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054, 265, filed on Feb. 9, 2005, which is herein incorporated by reference in its entirety. The handle 8 may instead, or also, include a connector or connectors suitable for receiving stored energy from an external source, such as a hose connected to a hospital utility source of pressurized gas or of vacuum, or an electrical cord connectable to a power source.

Operation

Referring to FIG. 7, in the course of a catheterization procedure, a sheath 48 is inserted through a passage 53 in tissue 52 such that one end of the sheath 48 enters an opening 54 in a blood vessel 56. The passage 53 extends between the epidermis 55 of the patient and the opening 54 in the blood vessel 56. The sheath 48 may be advanced any suitable distance into the blood vessel 56, as determined by the physician performing the procedure. As an example of a catheterization procedure, the blood vessel 56 may be a femoral artery, and the tissue 52 may be the tissue of the leg between the surface of the leg and the femoral artery. Femoral access to the vasculature, or similar access through another suitable blood vessel such as the radial artery, is standard. Referring also to FIG. 2, a guiding catheter 80, which is also standard, may be inserted through the introducer sheath 48 into the blood vessel 56, as may a guidewire. The guiding catheter 80 and at least one guidewire 82 are advanced through the vasculature to a location in proximity to the aneurysm 84. The guidewire 82 may be located within a lumen of the guiding catheter 80, or may extend distally from the end of the guiding catheter 80, during this advancement. Alternately, the guiding catheter 80 is not used, and the guidewire 82 is advanced through the vasculature of the patient by itself. The advancement of the guiding catheter 80 and at least one guidewire 82 advantageously may be performed with the assistance of a fluoroscope or other imaging device that indicates the position of the guiding catheter 80 and/or at least one guidewire 82 in the patient. The use of such an imaging device in conjunction with a guiding catheter 80 and/or at least one guidewire 82 is standard. The distal end of the guidewire and/or the distal end of the guiding catheter 80 may be advanced into the aneurysm 84. The guiding catheter 80 then may be withdrawn from the patient. Alternately, the guiding catheter 80 may be left in place, such as where the end effector 4 is attached to the guiding catheter 80.

The end effector 4 of the closure system 2 is then advanced along the guidewire 82, until the distal end of the end effector 4 and/or any items protruding from the distal end of the end effector 4 enters the aneurysm 84 and contacts the tissue and/or other material within. For this reason, the distal end of the end effector 4 and/or any items protruding from the distal end of the end effector 4 are advantageously blunt, to avoid causing injury at the aneurysm 84 upon contacting it. Contact between the distal end of the end effector 4 and/or any items protruding from the distal end of the end effector 4 stops the forward motion of the end effector 4, and indicates to the user that the end effector 4 is in position in the aneurysm 84. This position may be referred to as the standby position of the end effector 4. A fluoroscope or other imaging device may also be used to confirm that the end effector 4 is in the standby position. After the end effector 4 is in the standby position, the guidewire 82 may be left in place, or may be removed from the aneurysm 84. Contact between the distal end of the end effector 4 and the aneurysm 84, optionally coupled with gentle distal pressure exerted on the end effector 4, holds the end effector 4 substantially in the standby position. When the end effector 4 is in the standby position, at least part of the staple 24 is located within the aneurysm 84. Advantageously, the entire staple 24 is located within the aneurysm 84. However, at least part of the staple 24 may be located outside the aneurysm when the end effector 4 is in the standby position. At this time, the staple 24, 24a is in an initial position, as shown in FIGS. 5A and 6A.

After the user has confirmed that the end effector 4 is in the standby position, the staple 24, 24a is splayed outward without being ejected from the end effector 4, as shown in FIGS. 5B and 8. The driver 34 retracts proximally, and may be actuated to retract proximally in any suitable manner. As one example, the driver 34 is urged distally when the handle 8 exerts a proximal force on a cable (not shown) or other structure or mechanism connected to the driver 34. The handle 8 may exert such a force in any suitable manner, as described above. As another example, the driver 34 extends through the shaft 6 to the handle 8, and the driver 34 is actuated directly by a mechanism or mechanisms associated with the handle 8.

As the driver 34 retracts proximally, the raised area 74 of the driver 34 exerts a force in the proximal direction on the staple 24. Each post 41 of a paddle 40 restrains the corresponding valley 29 of the staple 24 substantially against proximal motion, such that the longitudinal position of the peaks 28 and the trough 30 of the staple are substantially unchanged as the raised area 74 of the driver 34 begins to exert a proximal force on the staple 24. However, the tines 26 of the staple 24 are not substantially restrained against motion resulting from application of force in the proximal direction. The proximal force exerted on at least one peak 28 of the staple 24 by the raised area 74 of the driver 34 urges each valley 29 of the staple 24 against the corresponding post 41 of the paddle 40. Each post 41 is positioned sufficiently far from the longitudinal centerline of the staple 24 such that a moment is generated about that post 41 that is applied to the corresponding peak 28 of the staple 24. This moment causes the corresponding tine 26 of the staple 24 to move outward from the longitudinal centerline of the staple 24. Each post 41 may be shaped, sized, positioned or otherwise configured in any manner that results in such a moment and the resultant motion of the tines 26 of the staple 24.

Thus, as the raised area 74 of the driver 34 exerts a force on the staple 24, the distal ends of the tines 26 of the staple 24 move apart from one another, each in a direction away from the longitudinal centerline of the staple 24. This deformation of the staple may be referred to as "splaying." During splaying of the staple 24, the tines 26 themselves may remain substantially undeformed; rather, a portion of the staple 24 in proximity to each peak 28 and/or the trough 30 may deform. Alternately, at least one tine 26 may deform during splaying of the staple 24. Further, as the distal ends of the tines 26 move away from the longitudinal centerline of the staple 24, at least part of each tine 26 may move outside the distal end of the housing 22 through a slot 23 or other opening in the housing 22. As a result, the tines 26 of the staple 24 may move apart from one another a distance greater than the diameter of the housing 22. Where the staple 24 is made from a plastically-deformable material such as stainless steel, the staple 24 deforms plastically as it splays from its initial configuration to the splayed configuration. Plastic deformation is deformation that remains after the load that caused it is removed, or that would remain if the load were removed. Alternately, the staple 24 is elastically-deformable from its initial configuration to the splayed configuration. The staple 24 may be spring-loaded inwards to the initial configuration, such that the staple 24 springs outward and returns to the splayed configuration upon application of force or upon movement to a position relative to the housing 22 such that the staple 24 is free to spring outward. Alternately, the staple 24 may be splayed in a different manner. As one example, the posts 41 may be moved proximally while the driver 34 retracts proximally, or while the driver 34 is substantially stationary relative to the staple 24. In this way, splaying results from force exerted on the staple 24 by relative motion of the posts 41 and/or the driver 34. As another example, motion of one or more other components of the end effector 4 causes splaying of the staple 24. Alternately, the staple 24 does not deform or move to a splayed configuration at all; rather, it transitions directly from the initial configuration to a closed configuration as described below. If the staple 24 does not deform or move to a splayed configuration, then the tines 26 may be spaced apart as far as possible within the housing 22 when the staple 24 is in the initial configuration, such that the tines 26 are farther apart from one another than shown in FIG. 5.

Figure 9:
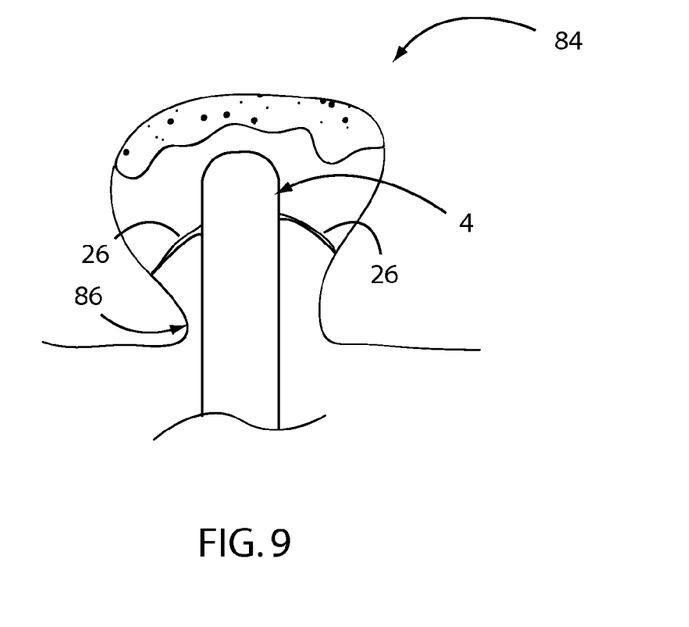
FIG. 9 is a side view of the splayed staple as it is retracted into tissue adjacent the neck of an aneurysm.

After the staple 24 has deformed to a splayed configuration, the raised area 74 of the driver 34 may stop applying force in the proximal direction on the staple 24. The staple 24 is still held by the end effector 4. Next, referring also to FIG. 9, the end effector 4 is retracted proximally until the tines 26 of the splayed staple 24 penetrate into tissue adjacent to the neck 86 of the aneurysm 84. The distal ends of the tines 26 are positioned further apart from one another when the staple 24 is in the splayed configuration than when the staple 24 is in the initial configuration, thereby allowing capture of tissue across a width greater than that of the housing 22 between the tines 26 as they enter and penetrate tissue 56. The staple 24 in the splayed configuration penetrates tissue 56 on opposite sides of the opening 86. Alternatively, more than one staple 24 may be deployed to close the opening 54. The user may confirm that the tines 26 have engaged that tissue in a tactile manner; the handle 8 may not move substantially proximally after such engagement.

Next, the posts 41 are moved away from the valleys 29 of the staple. As one example, the paddle assembly 38 is moved proximally relative to the driver 34, such that the posts 41 move in the proximal direction away from the staple 24. The anvil 78 may be positioned adjacent to the trough 30 of the staple 24, such that the staple 24 is held in place against the anvil 78 as a result of proximal force exerted by the raised area 74 in the proximal direction, or by simple contact between the staple 24 on the one hand and the anvil 78 and the raised area 74 of the driver 34 on the other. Optionally, the width of the driver 34 proximal to the wall 72 of the depression 70 may be less than the width of the driver 34 distal to the wall 72 of the depression 70. As another example, the posts 41 may be moved away from the plane in which the staple 24 generally lies, such as by moving the distal ends of the paddles 40 downward.

Next, the driver 34 moves proximally, applying compressive force to the staple 24 against the anvil 78. Each peak 28 of the staple 24 is offset from the longitudinal centerline of the staple 24. Further, the longitudinal centerline of the staple 24 substantially intersects or approaches close to intersection with the anvil 78. As a result, each peak 28 of the staple 24 is offset from the anvil 78. The force exerted by each bifurcation 76 of the raised area 74 of the driver 34 in the proximal direction on each peak 28, which is offset from the longitudinal centerline of the staple 24, results in a moment about the anvil 78. Each tine 26 of the staple 24 that experiences that moment moves toward the longitudinal centerline of the staple 24. In the course of this motion, the distal ends of the tines 26 may first move toward the longitudinal centerline of the staple 24 and toward one another, cross each other, then move away from the longitudinal centerline of the staple 24 and away from one another. The tines 26 need not substantially change shape as they move; rather, they may rotate about a pivot point located at or near the trough 30. Alternately, one or both of the tines 26 may deform as they move. The radius of curvature of each tine 26 may be substantially coincident with its path of travel during closure of the staple 24. Deformation of the staple 24 as a result of contact between the staple 24 and the projection 46 may be referred to as "closing" the staple 24. As the staple 24 closes, the tines 26 draw the edges of the neck 86 of the aneurysm 84 closer together.

Figure 10:
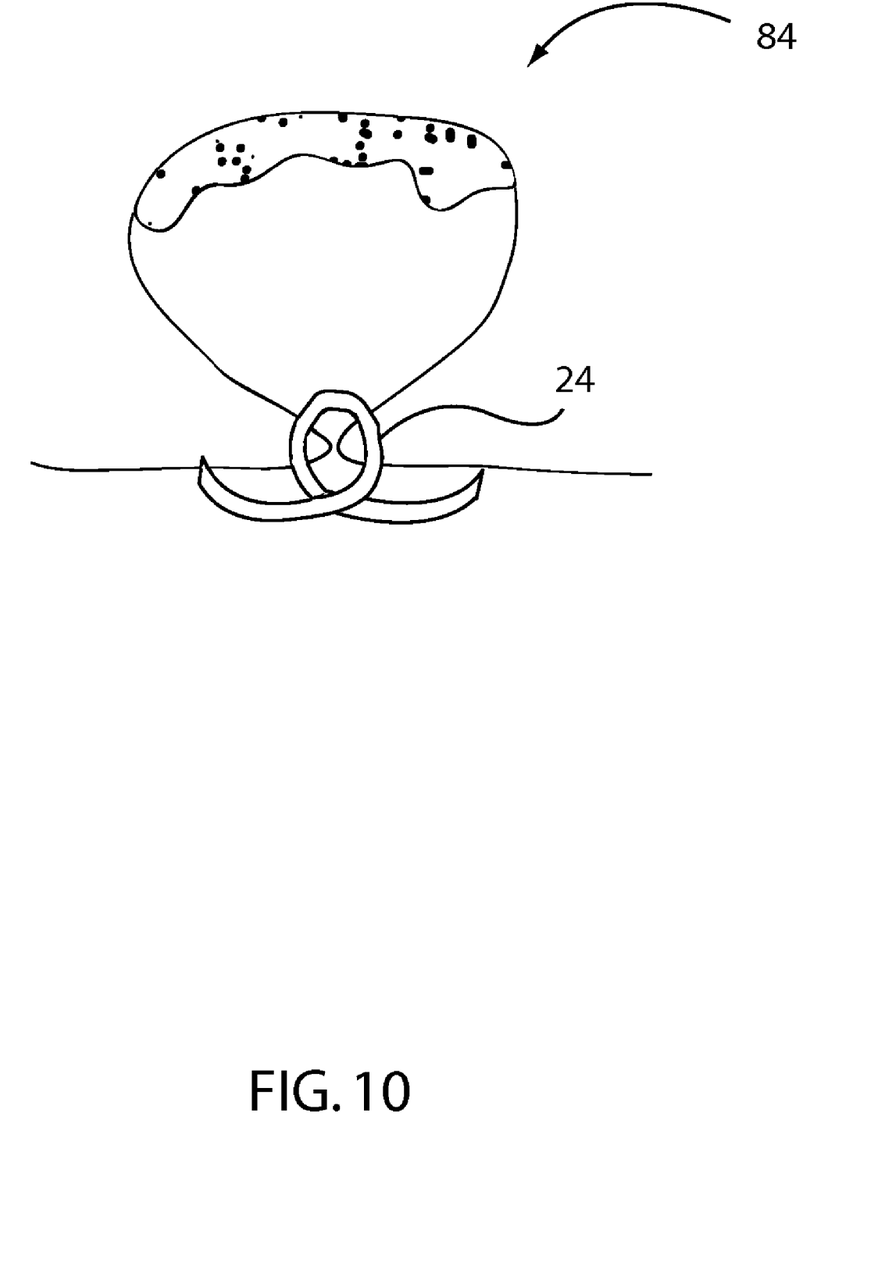
FIG. 10 is a perspective view of the end effector in a fourth configuration, as the staple is closed.

Referring also to FIGS. 5C and 10, as the driver 34 continues to move proximally, the staple 24, 24a continues to deform against the anvil 78. This deformation may be plastic deformation from the splayed configuration to a final, closed configuration. The staple 24 and/or any other component of the end effector 4 may be shaped or otherwise configured such that the tines 26 swipe past one another as the staple 24 moves to the closed configuration. Referring also to FIG. 5, as one example, the staple 24 is shaped such that the application of force longitudinally thereto causes the tines 26 to move in a direction that has a component of motion perpendicular to the longitudinal direction, thereby moving the tines 26 such that they swipe past each other. The staple 24 may be curved in any manner to allow for such motion of the tines 26. For example, the proximal surface 62 of the staple 24 may take the shape of a twisted plane, as described above. Contact between the driver 34 and the proximal surface 62 of the staple thus causes the tines 26 to move apart from one another in a direction perpendicular to the direction in which the legs move toward one another as the staple 24 moves to a closed configuration, such that the tines 26 swipe past one another as the staple 24 closes. That is, because the force applied to the proximal surface 62 of the staple 24 is substantially in the longitudinal direction, and the proximal surface 62 of the staple 24 is twisted such that lines perpendicular to that proximal surface 62 on opposite lateral sides of the staple 24 are skewed in opposite directions relative to the longitudinal direction, the force applied to the staple 24 tilts the tines 26 in opposite directions. Thus, when the staple 24 is closed, the tines 26 may be both offset from and substantially adjacent to one another. Alternately, at least two tines 26 of the staple 24 are configured to interfere with or otherwise engage one another when the staple 24 is in the closed position. Alternately, at least two tines 26 may be substantially parallel to one another and spaced apart from one another when the staple 24 is in the closed position.

Alternately, the distal ends of the tines 26 of the staple 24 are shaped substantially conically. As the staple 24 closes, the conical tips of the tines 26 come into contact with one another. As a result of the angle of the side of each conical tip, this contact causes the tines 26 to slide adjacent to one another instead of interfering with one another. Alternately, the end of each tine 26 is substantially planar, where each plane is oriented in a different direction. As a result, when the ends of the tines 26 encounter one another, contact between the differently-oriented planes at the distal ends of the tines pushes the tines 26 out of plane relative to one another. Alternately, the tines 26 of the staple 24 are fabricated such that they are out of plane with one another when the staple 24 is in the initial configuration, such that the tines 26 do not substantially interfere with one another during deployment. Alternately, the tines 26 of the staple 24 are plastically deformed out of plane with one another by contact with the paddle 40 while the staple 24 is splayed open and/or being closed. Alternately, the staple 24 and/or the end effector 4 are configured to prevent the tines 26 from interfering with one another as the staple 24 closes.

When deformation of the tines 26 of the staple is complete, the staple 24 is in the closed configuration. In that closed configuration, a portion of the staple 24 is located inside the aneurysm 84, and the tines 26 have drawn the edges of the neck 86 of the aneurysm 84 into apposition, or has brought them closer together, substantially closing the neck 86 and substantially isolating the aneurysm 84 from the vasculature. At least part of each tine 26 of the staple 24 is then located within the lumen of the blood vessel 56 from which the aneurysm 84 protrudes. The tines 26 may be positioned such that a part of each tine 26 is positioned against an inner surface of the blood vessel 56. Alternately, the tines 26 may be positioned differently relative to the wall of the blood vessel 56. Where the staple 24 is frangibly connected to the driver 34, force is exerted on the staple 24 when the staple 24 approaches or reaches the closed configuration, in order to separate the staple 24 from the driver 34 such as by fracturing, as shown in FIG. 5C. The force on the staple 24 may be provided in any suitable manner. As one example, the connection between the staple 24 and the driver 34 may be shaped and sized such that the forces exerted on the staple 24 to deform it to the closed configuration also cause the staple 24 to separate from the driver 34. Alternately, the staple 24 is not separated from the driver 34 until the staple 24 is ejected from the housing 22. Alternately, the staple 24 is separated from the driver 34 at any other suitable time during the deployment process.

After the staple 24 has been closed, the end effector 4 ejects the staple 24 or allows the staple 24 to passively slide out of the end effector 4. As one example, the driver 34 moves distally, and/or the anvil 78 moves out of plane and/or proximally relative to the closed staple 24, such that the staple 24 is no longer trapped between the driver 34 and the anvil 78. As a result, the closed staple 24 is free to slide out of the end effector 4 as the end effector 4 is retracted proximally. As another example, where the paddles 40 were previously deflected out of plane relative to the staple 24, the paddles 40 may be moved back toward that plane. Such motion actively pushes the staple 24 away from the driver 34 laterally, such that the closed staple 24 is free to exit the housing 22 of the end effector 4. The paddles 40 may be moved in such a direction by relative motion of the paddle assembly 38 and the driver 34, or in any other suitable manner. Optionally, any suitable dye may be released by the end effector 4 after the closure of the staple 24, to verify closure of the aneurysm 84. The dye may be held within the end effector 4 and released upon reception of an input from the handle 8 via the shaft 6, such as via a cable (not shown). Alternately, the dye may be injected or introduced into the shaft 6, after which the dye travels along the shaft 6 to the end effector 4 and is released through a port or aperture (not shown) in the end effector 4. A fluoroscope or other suitable imaging device is used to view the dye and determine if the dye is contained within the aneurysm 84, meaning that the aneurysm 84 is closed, or if the dye leaks out of the aneurysm 84, meaning that the aneurysm 84 is not closed.

Next, the end effector 4 is moved out of the closed aneurysm 84. The end effector 4 is pulled out of the aneurysm 84 adjacent to the closed staple 24 and between the edges of what had been the neck 86 of the aneurysm 84. The end effector 4 is small enough in cross-section to allow such removal while maintaining substantial closure of the neck 86 of the aneurysm 84 after removal of the end effector 4 therefrom. As the end effector 4 is moved away from the opening 54, the staple 24 exits the distal end of the housing 22, as it grasps the tissue 56 with greater force than any remaining frictional forces or other incidental forces holding it to the housing 22. Alternately, the end effector 4 is already located outside of the aneurysm 84 when the staple 24 has moved to the closed configuration. The end effector 4 is then removed from the patient. The guidewire 82, if used, is then removed from the blood vessel 56. Alternately, the guidewire 82 is removed at a different time. If the distal end of the guidewire 82 is still located in the aneurysm 84, the guidewire 82 is pulled out of the aneurysm 84 adjacent to the closed staple 24 and between the edges of what had been the neck 86 of the aneurysm 84. The catheter 80, if still present in the patient, is also removed. After the end effector 4 is removed from the patient, the sheath 48 is removed if it is still present in the patient. The procedure is complete, and the neck 86 of the aneurysm 84 is substantially closed.

The operation of the closure system 2 has been described above in an exemplary manner with regard to the closure of an aneurysm. However, the closure system 2 may be used to close any tubular tissue structure in a human or animal, if desired. The operation of the closure system 2 to close a tubular tissue structure is substantially as described above. The end effector 4 is placed in the lumen of a tubular tissue structure, and the staple 24 held by that end effector 4 is splayed. The end effector 4 is then retracted, causing the tines 26 of that splayed staple 24 to penetrate into the walls of the tubular tissue structure. When the staple 24 is closed, the tines 26 pull the walls of the tubular tissue structure into contact with one another, closing the lumen of that tubular tissue structure.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method for closing an aneurysm, the aneurysm having a neck connected to a blood vessel, comprising:
   providing a staple having a plurality of tines, said tines oriented at least partially in the proximal direction;
   advancing said staple through the vasculature to a location within the aneurysm;
   plastically deforming said staple to a splayed configuration;
   penetrating at least one said tine of said staple in said splayed configuration into tissue in proximity to the neck of the aneurysm
   plastically deforming said staple to a closed configuration, whereby the neck of the aneurysm is substantially closed; and providing an end effector, wherein said end effector holds said staple; and wherein said plastically deforming said staple to a splayed configuration and said plastically deforming said staple to a closed configuration are performed by said end effector.

2. The method of claim 1, further comprising
   providing a guidewire; and
   advancing said guidewire through the vasculature until the distal end of said guidewire is located within the aneurysm;
   wherein said advancing said staple is performed by advancing said end effector along said guidewire.

3. The method of claim 2, wherein said penetrating is caused by moving said staple proximally along said guidewire.

4. The method of claim 1, wherein said advancing comprises advancing said staple through the vasculature to a location completely within the aneurysm.

5. The method of claim 1, wherein said end effector includes a housing, further comprising passively ejecting said staple from said housing after said plastically deforming said staple to a closed configuration.

6. The method of claim 5, further comprising holding said staple completely within said housing before said plastically deforming said staple to said splayed configuration.

7. The method of claim 1, wherein said advancing is performed without a guidewire.

* * * * *